Figure 1:
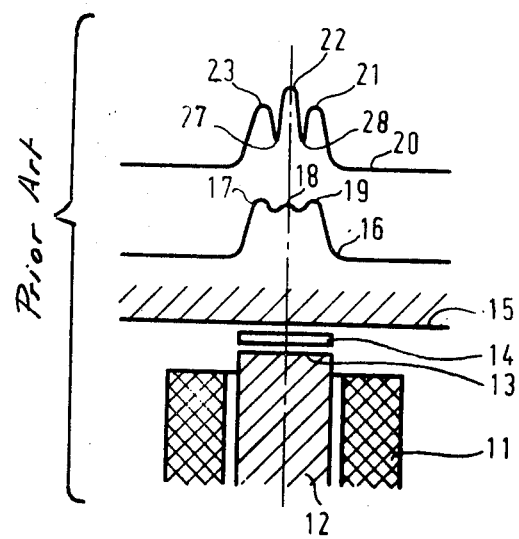

United States Patent [19]

Kopineck et al.

[11] 4,138,896
[45] Feb. 13, 1979

[54] ELECTRODYNAMIC SOUND CONVERTER

[75] Inventors: Hermann J. Kopineck; Wolfgang Böttcher, both of Dortmund, Fed. Rep. of Germany

[73] Assignee: Hoesch Werke Aktiengesellschaft, Dortmund, Fed. Rep. of Germany

[21] Appl. No.: 796,883

[22] Filed: May 16, 1977

[30] Foreign Application Priority Data

May 15, 1976 [DE] Fed. Rep. of Germany ....... 2621684

[51] Int. Cl.$^2$ .......................................... G01N 29/04
[52] U.S. Cl. ...................................................... 73/643
[58] Field of Search ....... 73/67.5 R, 67.8 R, 71.5 US, 73/643; 310/15; 324/207, 239, 240

[56] References Cited

U.S. PATENT DOCUMENTS

| | | |
|---|---|---|
| 3,460,063 | 8/1969 | Houck et al. .......................... 340/15 |
| 3,583,213 | 6/1971 | Houck et al. ...................... 73/67.5 R |
| 3,963,980 | 6/1976 | Shkarlet ............................... 324/239 |

FOREIGN PATENT DOCUMENTS

| | | | |
|---|---|---|---|
| 425201 | 2/1976 | United Kingdom ............... 73/71.5 US |
| 426716 | 1/1975 | U.S.S.R. ............................... 73/67.5 R |

*Primary Examiner*—Richard C. Queisser
*Assistant Examiner*—John P. Beauchamp
*Attorney, Agent, or Firm*—Walter Becker

[57] ABSTRACT

An electrodynamic sound converter which comprises a magnet adapted to generate a magnetic field and direct same onto the surface of the workpiece to be checked by the electrodynamic sound converter, and which also includes an excitation coil located between the magnet and the workpiece to be checked for generating electromagnetic oscillations. That end of the magnet core of the magnet which faces the workpiece to be checked is so designed that the magnet core decreases in cross section toward its foremost point which is closest to the surface of the workpiece to be checked, the rate of increase increasing in the direction toward the foremost point of the magnet core.

7 Claims, 2 Drawing Figures

ELECTRODYNAMIC SOUND CONVERTER

The present invention relates to an electrodynamic sound converter for generating and receiving ultrasonic waves as they are employed in particular for checking materials. Heretofore, for effecting a destruction-free examination of material, ultrasonic waves were generally generated in piezo-electric ultrasonic generators and were by said ultrasonic generators introduced into the material to be checked by means of a moistening coupling liquid, mostly of water or oil. In some instances, for instance when checking warm or hot workpieces, the employment of a coupling liquid is not desirable.

Therefore, attempts have been made to circumvent the just mentioned difficulties by a device which operates contact-free and which generates the ultrasonic waves directly in the workpiece to be checked, said device receiving the reflected ultrasonic waves in a contact-free manner. Devices of this type have become known as electrodynamic sound converters and are described for instance in German Pat. No. 14 97 777 as well as in U.S. Pat. No. 3,460,063-Houck, et al issued Aug. 5, 1969, U.S. Pat. No. 3,963,980—Shkarlet issued June 15, 1976 and British Pat. No. 1,425,201-Lewis dated Feb. 18, 1976. The devices consist of permanent- or electro magnet in the magnetic field of which a body with an electrical conducting upper surface is located by way of which with nominal spacing likewise in the region of the magnetic field there is provided a high frequency coil which is energized in a pulse manner by a high frequency oscillator whereby in the electrically conducting upper surface eddy currents are induced with the frequency of high frequency coil. A force is exerted upon the elementary particles through which the eddy currents flow because these are located in the magnetic field of the electro magnet. This force is known as a Lorenz force. The force continuously changes in direction corresponding to frequency of the current of the HF coil whereby the elementary particles of the electrically conducting upper surface having the eddy currents flow therein are energized to have mechanical ultra sonic oscillation corresponding to the frequency of the high frequency oscillator. The British Pat. No. 1,425,201 discloses advantageous modification for application of a magnetic field on one side with the aid of an electromagnet having a bar formed core and utilizing flat HF coils. A stronger concentration of magnetic field lines upon a small plane of outlet surface is known from the U.S. Pat. No. 3,963,980-Shkarlet.

The heretofore known electrodynamic sound converters have the drawback that similar to the piezo-electric ultrasonic generators, they have a short range field interfered with by interferences. This means that said known electrodynamic sound converters generate an approximately homogeneous ultrasonic wave front, as it is desired for the examination of the respective material, generally only in a relatively deep region below the surface of the workpiece to be examined. Therefore, with these known devices, the workpiece cannot be properly examined in the vicinity of the surface of said workpiece.

A further drawback of the heretofore known electrodynamic sound converters furthermore consists in that excitation distribution of the ultrasound field, in addition to the main maximum proper, has one or more secondary maxima which differ only slightly in height from said main maximum. As a result thereof, in said ultrasonic field areas are formed which have a considerably reduced ultrasonic intensity. It is in these areas that a reduced sensitivity exists for finding faults or flaws.

It is, therefore, an object of the present invention to considerably reduce the distance of the first uniform ultrasonic wave front (and therefore usable for the examination of the respective workpiece) from the workpiece surface and thus considerably to reduce the short range field which cannot be fully covered during the checking operation, and furthermore to generate a bundled excitation distribution of the ultrasonic field which is concentrated to form a narrow region around the ultrasonic field maximum and is free from secondary maxima.

These and other objects and advantages of the invention will appear more clearly from the following specification in connection with the accompanying drawing, in which:

FIG. 1 illustrates a heretofore known electrodynamic pulse echo sound converter with a plane end surface of the core and the curves pertaining to said core which curves illustrate the excitation distribution of the magnetic field and ultrasonic field strength.

Figure 2:
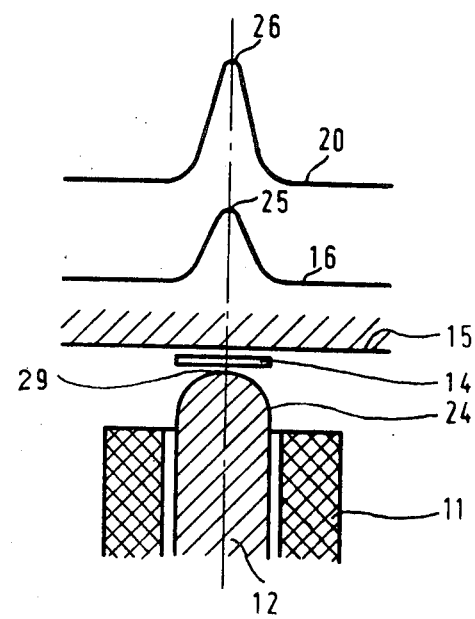

FIG. 2 diagrammatically illustrates an electrodynamic pulse echo sound converter according to the invention with a semispherical end surface of the magnetic core and with the curves pertaining thereto and indicating the excitation distribution of the magnetic field strength and ultrasonic field strength.

The electrodynamic pulse echo sound converter according to the present invention is characterized primarily in that that end of the core of the electromagnet which faces the workpiece is so designed that the core tapers to the outermost point which is closest to the workpiece surface while said reduction starts slightly at the circumference of the core and continuously increases toward said point which is closest to the workpiece surface.

In view of this particular shape of the end of the core of the electromagnet, the density of the magnetic lines of force is so distributed that an ultrasonic field is created which has a pronounced intensity maximum in its center and decreases toward the rims.

In this way, such a shape of the field intensity of the excitation distribution of the ultrasonic field is obtained which approaches that of the known Gaussian curve. Such a desired excitation distribution is obtained in a particularly advantageous form when the decrease occurs rotation symmetrically about the longitudinal axis and when with a section through the longitudinal axis of the core the generated outer limiting curves which represent the decrease follow a parabolic, elliptic, semicircular, circular or similar magnetic curve.

Referring now to the drawing in detail, the electrodynamic pulse echo sound converter shown in FIG. 1 comprises a coil 11 of the electromagnet with core 12 and energizing coil 14 energized by a non-illustrated high frequency oscillator. Coil 14 is located between the plane end 13 of the core 12 and the workpiece surface 15. With this example of the heretofore known principle, there is created a rotation symmetric excitation distribution of the magnetic field strength as it is illustrated in section by the curve 16. This section through the excitation distribution of the magnetic field strength shows three maximum values at the points 17, 18 and 19. The distribution of the magnetic field strength brings about a corresponding excitation distribution of the ultrasonic field strength as it is illustrated in curve 20 with its maximum values 21, 22 and 23 likewise shown as section. If a flaw in the workpiece is located within the region of one of the two minima 27 and 28, of curve 20, of the ultrasonic field strength, the sensitivity of proving a flaw is reduced. If such electrodynamic pulse echo sound converter would be moved over a minor flaw in a workpiece, successively three flaw indications were obtained which have their origin in the same flaw.

The interpretation of such flaw picture causes considerable difficulties in practice.

With the electrodynamic pulse echo sound converter of the present invention shown in FIG. 2, the end 24 of the core 12 is semispherical. That point of the core 12 which is closest to the workpiece surface 15 is designated with the reference numeral 29. The curve 16 of the excitation distribution of the magnetic field strength has only one maximum 25, and correspondingly, also the curve 20 of the excitation distribution of the ultrasonic field strength has only one maximum 26.

This design of the electrodynamic pulse echo sound converter brings about unequivocal flaw indications, especially for a good spatial resolution with regard to the location of minor flaws in the material and also permits a clear recognition of flaws in the surface near region, which means the conditions as they are necessary for a proper examination and interpretation of the result of such examination.

An electrodynamic pulse echo sound converter prepared in conformity with the principal of the present invention thus has a considerably greater resolution capability for small flaws in the workpiece than the heretofore known electrodynamic pulse echo sound converters ever had.

A further advantage of the sound converter according to the invention is obtained when the electromagnet with the coil 11 instead of a uniform direct current is excited by an intermittent direct current or alternating current of low frequency. In such an instance, the workpiece can during the turn-off intervals more easily be displaced in view of the absent magnet force. Furthermore, the coil 11 is less heated by the current with intermittent operation.

It is, of course, to be understood that the present invention is, by no means, limited to the specific showing in the drawing, but also comprises any modifications within the scope of the appended claims.

Thus, also cores 12 which are not extending at a right angle to the workpiece surface 15 can at the end be formed in such a way that an ultrasonic field is created which at its excitation approaches the Gaussian curve 20. The form of the magnet core 24 is at any rate a decrease in cross section which extends to the end and which is free from sharp edges or corners at its surface. This form of the core end differs from the above described shape all the more, the more the core 12 deviates from the plane perpendicular to the workpiece surface. The precise surface is easily ascertainable by a few tests or can be calculated by calculating the magnetic field.

What we claim is:

1. An electrodynamic pulse echo sound converter for transmitting and receiving sound pulses when checking materials, which includes in combination an electromagnet having a core with a front end portion having a foremost part to face the workpiece to be checked, said electromagnet being operable to generate a magnetic field and direct same onto the surface of a workpiece to be checked, and an excitation coil associated with said magnet and located in front of said front end of said core for generating oscillations, said front end portion of said core decreasing in cross section toward said foremost part with the rate of decrease increasing steadily toward said foremost part.

2. An electrodynamic pulse echo sound converter in combination according to claim 1, in which said decrease in cross section is rotationsymmetric with regard to the longitudinal axis of said core, the outer confining curves formed by the lines of intersection of a plane passing through the longitudinal axis of said core with the latter in the region of said front end portion having the approximate contour of a mathematical curve avoiding disturbing fields.

3. An electrodynamic pulse echo sound converter in combination according to claim 2, in which said mathematical curves are for a parabolum.

4. An electrodynamic pulse echo sound converter in combination according to claim 1, in which the intensity of the magnetic field is distributed so that narrowly restricted ultrasonic field distribution at least approximates the contour of a Gaussian curve.

5. An electrodynamic pulse echo sound converter in combination according to claim 2, in which said mathematical curves are for an ellipse.

6. An electrodynamic pulse echo sound converter in combination according to claim 2, in which said mathematical curves are for a circle.

7. An electrodynamic pulse echo sound converter in combination according to claim 2, in which said mathematical curves are for a semi-circle.